United States Patent
Nakamura et al.

(10) Patent No.: US 8,975,072 B2
(45) Date of Patent: Mar. 10, 2015

(54) HUMAN ERYTHROID PROGENITOR CELL LINE COMPRISING HPV E6/E7 OPERABLY LINKED TO AN INDUCIBLE PROMOTER AND METHOD FOR PRODUCING HUMAN ENUCLEATED RED BLOOD CELLS

(71) Applicant: Riken, Wako-shi, Saitama (JP)

(72) Inventors: Yukio Nakamura, Tsukuba (JP); Ryo Kurita, Tsukuba (JP)

(73) Assignee: Riken, Saitama (JP)

( * ) Notice: Subject to any disclaimer, the term of this patent is extended or adjusted under 35 U.S.C. 154(b) by 22 days.

(21) Appl. No.: 13/745,178

(22) Filed: Jan. 18, 2013

(65) Prior Publication Data

US 2014/0024118 A1    Jan. 23, 2014

(30) Foreign Application Priority Data

Jul. 20, 2012   (JP) ................................. 2012-161878

(51) Int. Cl.
| | |
|---|---|
| *C12N 5/02* | (2006.01) |
| *C12N 5/07* | (2010.01) |
| *C12N 15/85* | (2006.01) |
| *C12N 15/86* | (2006.01) |
| *C12N 5/078* | (2010.01) |

(52) U.S. Cl.
CPC ............... *C12N 15/85* (2013.01); *C12N 15/86* (2013.01); *C12N 2710/20022* (2013.01); *C12N 2740/15043* (2013.01); *C12N 2830/003* (2013.01); *C12N 5/0641* (2013.01); *C12N 2501/105* (2013.01); *C12N 2501/125* (2013.01); *C12N 2501/14* (2013.01); *C12N 2501/165* (2013.01); *C12N 2501/39* (2013.01); *C12N 2501/60* (2013.01); *C12N 2502/1394* (2013.01); *C12N 2506/45* (2013.01); *C12N 2510/00* (2013.01)
USPC ........... 435/377; 435/384; 435/385; 435/386; 435/387; 435/372

(58) Field of Classification Search
CPC ...................... C12N 2501/125; C12N 2501/23; C12N 5/0647; C12N 2501/14; C12N 5/0641; C12N 5/0678; C12N 15/86; C12N 2740/16043; C12N 2800/108; C12N 7/00; C12N 2800/30; C12N 2830/00; C12N 2830/008; C12N 2830/85; C12N 2510/02; C12N 15/85
See application file for complete search history.

(56) References Cited

U.S. PATENT DOCUMENTS

| | | |
|---|---|---|
| 2007/0218552 A1 | 9/2007 | Giarratana et al. |
| 2011/0086424 A1 | 4/2011 | Lanza et al. |

FOREIGN PATENT DOCUMENTS

| | | |
|---|---|---|
| WO | 2005/118780 A1 | 12/2005 |
| WO | 2009/137629 A2 | 11/2009 |

OTHER PUBLICATIONS

Mouthon et al. Expression of tal-1 and GATA-Binding Proteins During Human Hematopoiesis. Blood, 1993, vol. 81, pp. 647-665.*
Wong et al. Establishment of an erythroid cell line from primary CD36+ erythroid progenitor cells Experimental Hematology, 2010, vol. 38, pp. 994-1005.*
Nakamura, "Artificial Production of Red Blood Cells", The Lecture Meeting Related to Blood of the Joint Transfusion Committee in Aichi Prefecture, Riken Bioresource Center Cell Bank, Aichi Industry & Labor Center (Japanese), Jan. 21, 2012.
Nakamura, "Artificial Production of Red Blood Cells", The Lecture Meeting Related to Blood of the Joint Transfusion Committee in Aichi Prefecture, Riken Bioresource Center Cell Bank, Aichi Industry & Labor Center (English), Jan. 21, 2012.
Takashi Hiroyama, et al., "Establishment of Mouse Embryonic Stem Cell-Derived Erythroid Progenitor Cell Lines Able to Produce Functional Red Blood Cells", PloS ONE, Feb. 2008, pp. 1-11, vol. 3, Issue 2.

\* cited by examiner

*Primary Examiner* — Deborah Crouch
(74) *Attorney, Agent, or Firm* — Sughrue Mion, PLLC

(57) ABSTRACT

Provided are: a method for producing an immortalized human erythroid progenitor cell line, enabling efficient and stable production of enucleated red blood cells; and a method for producing human enucleated red blood cells from a human erythroid progenitor cell line obtained by the aforementioned production method. An expression cassette capable of inducing expression of HPV-E6/E7 genes in the presence of DOX was introduced into the genomic DNA of blood stem cells. Then, the blood stem cells were cultured in the presence of DOX and a blood growth factor. Thereby, immortalized cell lines of human erythroid progenitor cells were established. Further, it was revealed that culturing the cell lines under a condition where the expression of the HPV-E6/E7 genes was not induced enabled differentiation induction into enucleated red blood cells at a high ratio.

8 Claims, 9 Drawing Sheets

HUMAN ERYTHROID PROGENITOR CELL LINE COMPRISING HPV E6/E7 OPERABLY LINKED TO AN INDUCIBLE PROMOTER AND METHOD FOR PRODUCING HUMAN ENUCLEATED RED BLOOD CELLS

BACKGROUND OF THE INVENTION

1. Field of the Invention

The present invention relates to a human erythroid progenitor cell line and a method for producing human enucleated red blood cells. More specifically, the present invention relates to a method for producing immortalized human erythroid progenitor cells (human erythroid progenitor cell line) from human blood stem cells, and a method for producing human enucleated red blood cells from a human erythroid progenitor cell line obtained by the aforementioned production method.

2. Related Background Art

The transfusion medical system has been established based on blood donation, and the system is well organized at present. However, this does not mean the system has no problem at all. One is a problem of relatively fewer donors because of population aging with declining birth rate. There is a concern about shortage of transfusion products in the future. Additionally, at the early stage of infection with hepatitis viruses, AIDS viruses, and the like, it is not always possible to determine that the patient is positive by the inspection. Accordingly, it is difficult to completely identify persons infected with these viruses and to completely eliminate the possibility that an infectious virus carrier is a blood donor. Thus, in the blood donation system from an unspecified number of donors, it is difficult to completely eliminate a risk of infectious diseases in reality. In addition, the cause of recently-defined transfusion related acute lung injury (TRALI) is believed to be an antibody present in a transfusion product. Therefore, if it becomes possible to artificially produce red blood cells from resources, for example, stem cells or immortalized cell lines, with ensured safety, it is likely to solve the existing problems such as risks of infectious diseases and TRALI.

Another reason why the artificial red blood cells production is eagerly desired comes from the necessity of guaranteeing transfusion medicine with very rare blood types. For example, persons having red blood cells without a red blood cell antigen most people in the world have (persons with type Rh-null, type -D-, or the like) need to be transfused with red blood cells not having such an antigen. For persons having such a special blood type, a strategy is conceivable, in which iPS cells are first established from such a person him/herself and blood in need is then artificially produced from the iPS cells thus established.

Now, red blood cells can be produced from pluripotent stem cells such as ES cells and iPS cells; specifically, mature red blood cells (enucleated red blood cells) can be produced in vitro through differentiation of pluripotent stem cells into blood stem cells further to erythroid progenitor cells (International Publication No. WO2009/137629). Moreover, it is also possible to produce enucleated red blood cells from umbilical cord blood-derived blood stem cells or other origins through erythroid progenitor cells (International Publication No. WO2005/118780).

However, in these methods, large amounts of various growth factors and so forth are needed to induce differentiation of pluripotent stem cells or blood stem cells into enucleated red blood cells, requiring high cost. This is because in a case of inducing differentiation of pluripotent stem cells, cells other than blood cells are also included at the early stage after the differentiation induction, and a long culturing period and a large culture volume are needed to obtain a required amount of blood cells. Meanwhile, in a case of using either blood stem cells induced and differentiated from pluripotent stem cells or blood stem cells derived from umbilical cord blood or other origins, when the blood stem cells are induced to differentiate into erythroid cells, blood cells other than erythroid cells are also included at the early stage after the differentiation induction.

Hence, it is necessary for obtaining a required red blood cell volume to culture for a long culturing period and culture in a large. Thus, to produce artificial red blood cells, a development has been demanded in a method that enables efficient and stable production of enucleated red blood cells.

In view of such a circumstance, the present inventors have attempted to establish, as immortalized cell lines having a semi-permanent growth potential, erythroid progenitor cells immediately before differentiation into red blood cells. As a result, by in vitro differentiation-induction manipulation, such immortalized cell lines of erythroid progenitor cells were successfully obtained from mouse ES cells. Further, the present inventors have also revealed that the cell lines are able to stably and efficiently produce enucleated red blood cells (Hiroyama T. et al., "Establishment of mouse embryonic stem cell-derived erythroid progenitor cell lines able to produce functional red blood cells," PLoS One, Feb. 6, 2008, vol. 3, issue 2, e1544).

SUMMARY OF THE INVENTION

As described above, the present inventors have established cell lines of erythroid progenitor cells from mouse ES cells, and have successfully obtained enucleated red blood cells from the cell lines. Nevertheless, no immortalized erythroid progenitor cell line (human erythroid progenitor cell line) capable of producing enucleated red blood cells has not been established from human pluripotent stem cells by the same method.

The present invention has been made in view of the problems of the conventional techniques. An object of the present invention is to provide a method for producing a human erythroid progenitor cell line capable of efficiently and stably producing human enucleated red blood cells, and a method for producing human enucleated red blood cells from a human erythroid progenitor cell line obtained by the aforementioned production method.

The present inventors have earnestly studied in order to achieve the above objects. First, an expression cassette capable of inducing expression of E6 and E7 genes of human papillomavirus type 16 (HPV-E6/E7 genes) in the presence of doxycycline (DOX) was introduced into the genomic DNA of human umbilical cord blood-derived or iPS cell-derived blood stem cells. Next, the human blood stem cells capable of stably expressing HPV-E6/E7 genes in the presence of DOX were cultured in the presence of DOX and blood growth factors (human stem cell factor (SCF), human erythropoietin (EPO), and dexamethasone (DEX)). Thus, the present inventors successfully established immortalized cell lines of human erythroid progenitor cells.

Further, the dependency on DOX (expression of the HPV-E6/E7 genes) and the blood growth factors was analyzed in the growth of the established human erythroid progenitor cell lines. As a result, it was found out that HPV-E6/E7 expression and predetermined blood growth factors were essential for the growth of the cell lines. Meanwhile, it has been known that, in the differentiation and maturation processes of red blood cells, the cell division potential is gradually decreased from the stage of erythroid progenitor cells, and orthochromatic erythroblasts before enucleation at the final stage lose the cell division potential completely.

Hence, the inventors thought that decreasing the cell growth potential could efficiently induce differentiation into matured red blood cells, and attempted to induce differentiation into mature erythroid cells (including enucleated red blood cells) by culturing under a condition excluding HPV-E6/E7 and the blood growth factors essential for the growth of the human erythroid progenitor cell lines.

As a result, it was found out that the erythroid cells thus obtained included enucleated red blood cells at a high ratio, and further that hemoglobins of the cell lines of human erythroid progenitor cells had a similar function to that in normal red blood cells in terms of oxygen binding and releasing ability. This discovery has led to the completion of the present invention.

Specifically, the present invention provides the followings.
<1> A method for producing a human erythroid progenitor cell line for producing human enucleated red blood cells, the method comprising the steps of:
introducing into human blood stem cells an expression cassette capable of inducing expression of E6 and E7 genes of human papillomavirus type 16 in response to an external stimulus; and
culturing the human blood stem cells having the expression cassette introduced therein in presence of an external stimulus and a blood growth factor.
<2> The method according to <1>, wherein the human blood stem cells are cells obtained by inducing differentiation of human pluripotent stem cells expressing a TAL1 gene.
<3> A human erythroid progenitor cell line comprising an expression cassette capable of inducing expression of E6 and E7 genes of human papillomavirus type 16 in response to an external stimulus, wherein the human erythroid progenitor cell line grows in presence of the external stimulus and a blood growth factor and has a potential to produce human enucleated red blood cells by culturing in absence of the external stimulus.
<4> A method for producing human enucleated red blood cells, the method comprising the step of culturing the human erythroid progenitor cell line obtained by the method according to any one of <1> and <2> or the human erythroid progenitor cell line according to <3> in absence of the external stimulus.
<5> A method for producing human enucleated red blood cells, the method comprising the steps of:
introducing into human blood stem cells an expression cassette capable of inducing expression of E6 and E7 genes of human papillomavirus type 16 in response to an external stimulus;
culturing the human blood stem cells having the expression cassette introduced therein in presence of an external stimulus and a blood growth factor to obtain human erythroid progenitor cells; and
culturing the human erythroid progenitor cells in absence of the external stimulus.
<6> The method according to <5>, wherein the human blood stem cells are cells obtained by inducing differentiation of human pluripotent stem cells expressing a TAL1 gene.
<7> A human erythroid stem cell comprising an expression cassette capable of inducing expression of E6 and E7 genes of human papillomavirus type 16 in response to an external stimulus.

<8> The human erythroid stem cell according to <7>, wherein the human blood stem cell is a cell obtained by inducing differentiation of human pluripotent stem cells expressing a TAL1 gene.

The present invention makes it possible to provide a method for producing a human erythroid progenitor cell line capable of efficiently and stably producing human enucleated red blood cells, and a method for producing human enucleated red blood cells from a human erythroid progenitor cell line obtained by the aforementioned production method.

DETAILED DESCRIPTION OF THE PREFERRED EMBODIMENTS

Figure 1:
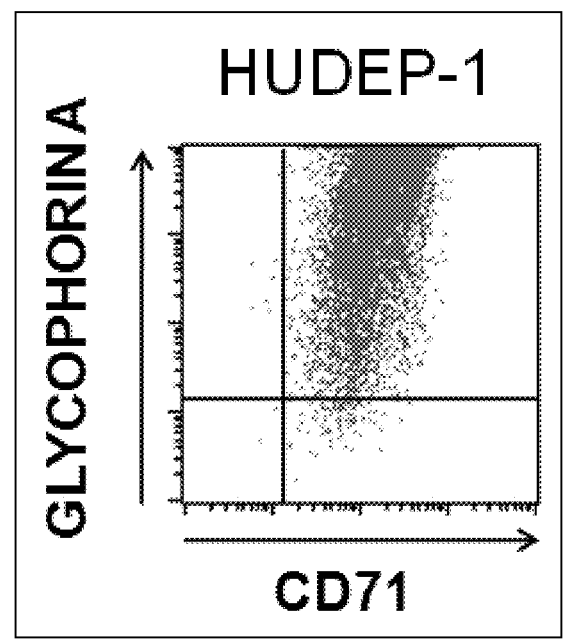
FIG. 1 is a plot chart for illustrating the result of analyzing, with a flow cytometer, expression of CD71 and glycophorin A in a cell line (HUDEP) of human erythroid progenitor cells obtained from human umbilical cord blood-derived blood stem cells by a production method of the present invention.

<Method for Producing Human Erythroid Progenitor Cell Line>

In a method for producing a human erythroid progenitor cell line of the present invention, first, an expression cassette capable of inducing expression of E6 and E7 genes of human papillomavirus (HPV) type 16 in response to an external stimulus is introduced into human blood stem cells.

In the present invention, "erythroid progenitor cells" mean cells having a differentiation potential to only mature red blood cells and no differentiation potential to other blood cells. Moreover, an "erythroid progenitor cell line" means immortalized erythroid progenitor cells, which can repeat cell division limitlessly.

In the present invention, "blood stem cells" mean stem cells having no differentiation potential to cells other than blood cells but having a differentiation potential to all types of blood cells. "Blood stem cells" are also called "hematopoietic stem cells." Such "blood stem cells" are known to be abundantly included in a cell population separated and collected from a tissue, such as umbilical cord blood, peripheral blood, bone marrow, or fetal liver, by flow cytometry or the like using an antibody specifically binding to a surface antigen (such as CD34) on hematopoietic stem cells. Further, in the present invention, "blood stem cells" can also be prepared by inducing differentiation of human pluripotent stem cells as described later.

The "human pluripotent stem cells" according to the present invention may be any cells, as long as the cells can self-renew and be induced to differentiate into blood stem cells. Examples of such cells include cells that can be collected in vivo, such as embryonic stem cells (ES cells), embryonal carcinoma cells (EC cells), embryonic germ cells (EG cells), multipotent germline stem cells (mGS cells), mesodermal stem cells, mesenchymal stem cells, and MUSE cells (see Kuroda Y. et al, Proc. Natl. Acad. Sci. U.S.A., 2010, vol. 107, no. 19, pp. 8639 to 8643). Moreover, an example of the cells also includes cells artificially prepared in such a manner as to have differentiation pluripotency, such as iPS cells. Among these, iPS cells are excellent and suitably used as the pluripotent stem cells according to the present invention from an ethical viewpoint that the cells can be prepared without destroying an embryo and further from the viewpoint that for use in transfusion or the like, the iPS cells make it easy to match the blood type (red blood cell antigen) of a patient to be transfused.

Further, the "human pluripotent stem cells" according to the present invention are preferably human pluripotent stem cells expressing a TAL1 gene from the viewpoint of more improved efficiency of inducing differentiation into blood cells (particularly erythroid cells). Examples of a method for preparing the human pluripotent stem cells expressing a TAL1 gene include: a method in which genes used to prepare iPS cells (for example, Klf4, Oct3/4, Sox2, c-Myc) are introduced together with the TAL1 gene into somatic cells; a method in which the TAL1 gene is introduced into already established iPS cells; a method in which genes used to prepare iPS cells (for example, Klf4, Oct3/4, Sox2, c-Myc) are introduced into cells expressing the TAL1 gene at high level; and the like.

Note that the TAL1 (T-cell acute lymphocytic leukemia 1) gene is a gene also called an SCL (stem cell leukemia hematopoietic transcription factor) gene and a TCL5 (T-cell leukemia 5) gene. Typically, the gene is a nucleic acid (for example, DNA having a base sequence of SEQ ID NO: 1) encoding a protein having an amino acid sequence of SEQ ID NO: 2.

The method for inducing differentiation of the human pluripotent stem cells to human blood stem cells further to erythroid cells is not particularly limited. For example, as described in Examples later, first, human pluripotent stem cells are co-cultured with feeder cells in the presence of human insulin-like growth factor-II (IGF-II) and human vascular endothelial growth factor (VEGF) to induce differentiation into blood cells including blood stem cells. Then, for example, by co-culturing with feeder cells in the presence of human stem cell factor (SCF), human erythropoietin (EPO), and dexamethasone (DEX) in place of IGF-II and VEGF, differentiation into a cell population including erythroid cells abundantly can be induced.

In such differentiation induction, a culture solution supplemented with the above IGF-II, VEGF, SCF, EPO, and DEX is used. As the culture solution, a "blood stem/progenitor cell-differentiation induction culture solution" described in Examples later or other known culture solutions can be selected as appropriate for use. Additionally, as the feeder cells used in the co-culturing with human pluripotent stem cells and the like, OP9 cells or other known feeder cells can be selected as appropriate for use.

The "expression cassette capable of inducing expression of E6 and E7 genes (HPV-E6/E7 genes) of human papillomavirus (HPV) type 16 in response to an external stimulus," which is to be introduced into the human blood stem cells is a nucleic acid construct comprising: a promoter capable of inducing expression of a downstream gene in response to an external stimulus; HPV-E6/E7 genes whose expression is controlled by the promoter; and a terminator.

The "HPV-E6/E7 genes" are typically a nucleic acid (for example, DNA having a base sequence of SEQ ID NO: 3) encoding a protein (HPV-E6 protein) having an amino acid sequence of SEQ ID NO: 4 and a protein (HPV-E7 protein) having an amino acid sequence of SEQ ID NO: 5.

The promoter is not particularly limited, as long as the promoter is capable of inducing expression of the downstream gene in response to an external stimulus. An example thereof includes: a promoter capable of inducing expression of the downstream gene by binding to a complex including a tetracycline antibiotic (tetracycline, doxycycline, or the like) and a tetracycline transactivator in a case where the external stimulus is the presence of the tetracycline antibiotic; a promoter capable of inducing expression of the downstream gene by release of a tetracycline repressor in a case where the external stimulus is the absence of a tetracycline antibiotic; a promoter capable of inducing expression of the downstream gene by binding of an ecdysteroid (ecdysone, muristerone A, ponasterone A, or the like) to an ecdysone receptor-retinoid receptor complex in a case where the external stimulus is the presence of the ecdysteroid; and a promoter capable of inducing expression of the downstream gene by binding of FKCsA to a complex including a Gal4 DNA binding domain fused to FKBP12 and a VP16 activator domain fused to cyclophilin in a case where the external stimulus is the presence of FKCsA.

The expression cassette may comprise, as necessary, an enhancer, a silencer, a selection marker gene (for example, a drug resistance gene such as a neomycin resistance gene), an SV40 replication origin, and the like. Further, those skilled in the art could construct an expression cassette capable of inducing expression of the HPV-E6/E7 genes at a desired expression level by appropriately selecting a combination of known enhancers, silencers, selection marker genes, terminators, and so forth in consideration of the type of the promoter utilized and so on.

In addition, as necessary, into the human blood stem cells according to the present invention, an expression cassette may also be introduced, which is capable of constantly expressing in the nucleus a factor (for example, tetracycline transactivator, a tetracycline repressor, an ecdysone receptor-retinoid receptor complex, a complex including a Gal4 DNA binding domain fused to FKBP12 and aVP16 activator domain fused to cyclophilin) for inducing expression of the HPV-E6/E7 genes in response to an external stimulus.

In the present invention, a method for introducing the expression cassette into the human blood stem cells is not particularly limited, a known approach can be selected as appropriate for use. For example, the expression cassette may be inserted in an appropriate expression vector to introduce the expression vector into the cells by infection, lipofection, liposome transfection, electroporation, calcium phosphate coprecipitation, DEAE-dextran transfection, and microinjection.

Examples of such an expression vector include animal cell expression plasmids and viral vectors such as lentiviruses, retroviruses, herpesviruses, adenoviruses, adeno-associated viruses, and Sendai virus. From the viewpoint of quite high introduction efficiency into the genomic DNA of blood stem cells not having so high a growth activity, lentiviruses are preferable.

The "human blood stem cells having the expression cassette introduced therein" thus obtained are human blood stem cells capable of stably expressing the HPV-E6/E7 genes in the presence of the external stimulus as a result of introducing the expression cassette according to the present invention into the cells. Moreover, from the viewpoint that the expression cassette according to the present invention can be removed together with the nuclei at the establishment stage of the cell line and further at the differentiation stage into human enucleated red blood cells described later, the human blood stem cells are preferably human blood stem cells comprising the expression cassette according to the present invention incorporated into the genomic DNA.

In the method for producing a human erythroid progenitor cell line of the present invention, next, the human blood stem cells having the expression cassette introduced therein are cultured in presence of the external stimulus and a blood growth factor.

In the present invention, a "blood growth factor" means a factor contributing to the differentiation induction from the blood stem cells into erythroid progenitor cells or growth of the erythroid progenitor cells. Examples of such a "blood growth factor" include SCF, EPO, TPO (thrombopoietin), and DEX.

In a culture solution described later, a suitable concentration of SCF added is 50 to 100 ng/ml, a suitable concentration of EPO added is 3 to 5 U/ml, a suitable concentration of TPO added is 50 to 100 ng/ml, and suitable concentration of DEX added is in the order of $10^{-6}$ M.

Meanwhile, those skilled in the art could appropriately adjust an amount of the external stimulus added to a medium described later, in consideration of the type of the promoter utilized and so on. For example, in a case where the external stimulus is the presence of doxycycline, a suitable concentration of doxycycline added is 1 to 2 µg/ml.

Examples of the culture solution, which is used for differentiation induction into the human erythroid progenitor cells, and which is supplemented with the external stimulus and the blood growth factor, include an IMDM solution, an α-MEM solution, and a DMEM solution. Further, the culture solution may contain fetal bovine serum (FBS), bovine serum albumin (BSA), human insulin, human transferrin, 2-mercaptoethanol, sodium selenate, ascorbic acid, alpha-monothioglycerol, L-glutamine, or the like. Furthermore, as necessary, an inorganic salt (such as ferrous sulfate), an antibiotic (such as, for example, streptomycin, penicillin), or the like may be supplemented.

When a "blood cell population including blood stem cells derived from the human pluripotent stem cells" or a "blood cell population including abundantly blood stem cells derived from human umbilical cord blood or the like" is induced to differentiate into the erythroid progenitor cells, it is suitable to use, for example, an IMDM solution containing FBS, human insulin, human transferrin, sodium selenate, ascorbic acid, alpha-monothioglycerol, L-glutamine, and the like. Meanwhile, in consideration of clinical application of the cultured cells, a serum-free culture solution (culture solution not containing FBS) is preferable. As the serum-free culture solution for inducing differentiation into the erythroid progenitor cells, it is suitable to use, for example, an IMDM solution containing BSA, human insulin, human transferrin (human iron-saturated (holo) transferrin) and 2-mercaptoethanol (more specifically, "STEMSPAN® SFEM" manufactured by STEMCELL THECHNOLOGIES INC).

In the presence of the external stimulus and the blood growth factor, the culturing of the erythroid progenitor cells is continued while the culture solution is replaced. The culturing period during which an immortalized cell line is considered to be established is preferably 3 months. More preferably, an immortalized cell line is determined to be established when the cultured is continued for 6 months.

Further, from the viewpoint of having a sufficient period for stably introducing the expression cassette in the genomic DNA of the blood stem cells, the culturing may be performed in the absence of the external stimulus but in the presence of the blood growth factor for 1 to 7 days after the introduction of the expression cassette into the blood stem cells and before the culturing in the presence of the external stimulus and the blood growth factors.

Furthermore, the culturing during the differentiation induction from the human pluripotent stem cells into blood cells including the blood stem cells and the culturing until an immortalized cell line is obtained by subculturing blood cells and the like induced and differentiated from the human pluripotent stem cells are preferably co-culturing with feeder cells. Examples of the feeder cells include OP9 cells, MEF, SNL76/7 cells, PA6 cells, NIH3T3 cells, M15 cells, 10T1/2 cells, and the like. These feeder cells are preferably used after exposed to radiation or treated with a cell division inhibitor (such as mitomycin C) to stop the cell division.

<Method for Producing Human Enucleated Red Blood Cells>

As described in Examples later, the expression of HPV-E6/E7 genes is necessary for growth of the established erythroid progenitor cell line. Meanwhile, it has been known that, in the differentiation and maturation processes of red blood cells, the cell division potential is gradually decreased from the stage of erythroid progenitor cells, and orthochromatic erythroblasts before enucleation at the final stage lose the cell division potential completely. Thus, a method for producing human enucleated red blood cells of the present invention is provided from the viewpoint that a decrease in the cell growth potential efficiently induces differentiation into enucleated red blood cells.

Specifically, the method for producing human enucleated red blood cells of the present invention is a method comprising the step of culturing the human erythroid progenitor cell line produced by the above-described method in absence of the external stimulus.

Examples of a medium, which is used for the differentiation induction into the enucleated red blood cells, and from which the external stimulus is excluded, include an IMDM solution, an α-MEM solution, and a DMEM solution. Such mediums may contain human plasma protein fraction, human serum, D-mannitol, adenine, sodium hydrogen phosphate, mifepristone, α-tocopherol, linoleic acid, cholesterol, sodium selenite, human holo-transferrin, human insulin, ethanolamine, 2-mercaptoethanol, EPO, TPO, SCF, or the like. Further, as necessary, an inorganic salt or an antibiotic may be supplemented.

As described in Examples later, it has been revealed that SCF is also essential besides the external stimulus for the growth of human umbilical cord blood-derived erythroid progenitor cells of the present invention. Further, it has also been revealed that although EPO is not essential, the growth is improved in the presence of EPO. Meanwhile, it has been known that, in the differentiation and maturation processes of red blood cells, the cell division potential is gradually decreased from the stage of erythroid progenitor cells, and orthochromatic erythroblasts before enucleation at the final stage lose the cell division potential completely.

Thus, from the viewpoint that a decrease in the cell growth potential efficiently induces differentiation into enucleated red blood cells, for example, a medium having the following composition but not containing SCF is suitably used in the differentiation induction of the human umbilical cord blood-derived erythroid progenitor cells of the present invention into the enucleated red blood cells.

An IMDM solution containing human serum, α-tocopherol, linoleic acid, cholesterol, sodium selenite, human holo-transferrin, human insulin, ethanolamine, 2-mercaptoethanol, D-mannitol, and mifepristone.

Furthermore, the medium may contain 3 to 5 IU/ml of EPO from the viewpoint of suppressing cell death due to the differentiation induction, in other words, improving the cell survival rate at the stage of the differentiation induction.

Moreover, as described in Examples later, it has been revealed that EPO is also essential besides the external stimulus for the growth of human pluripotent stem cell-derived erythroid progenitor cells of the present invention. Thus, from the above-described viewpoint, for example, a medium having the following composition but not containing EPO is suitably used in the differentiation induction of the human pluripotent stem cell-derived erythroid progenitor cells of the present invention into the enucleated red blood cells.

An IMDM solution containing human plasma protein fraction, D-mannitol, adenine, sodium hydrogen phosphate, and mifepristone.

Additionally, the period of culturing the human erythroid progenitor cell line of the present invention in the absence of the external stimulus is normally 1 to 7 days, preferably 3 to 5 days, from the viewpoint of inducing and completing the enucleation while maintaining the cell survival rate.

Hereinabove, the description has been given of a preferred embodiment of the method for producing human enucleated red blood cells of the present invention, but the method for producing human enucleated red blood cells of the present invention is not limited to the above embodiment. For example, according to the following method, human enucleated red blood cells can be produced from human blood stem cells without establishing the above-described human erythroid progenitor cell line.

A method for producing human enucleated red blood cells, the method comprising the steps of:

introducing into human blood stem cells an expression cassette capable of inducing expression of E6 and E7 genes of human papillomavirus type 16 in response to an external stimulus;

culturing the human blood stem cells having the expression cassette introduced therein in presence of an external stimulus and a blood growth factor to obtain human erythroid progenitor cells; and culturing the human erythroid progenitor cells in absence of the external stimulus.

Note that those skilled in the art could carry out this production method also, while referring to the above description of the present invention and specific description of Examples, by appropriately selecting the configuration of the expression cassette according to the present invention, the method for introducing the expression cassette, culture conditions (for example, the composition of the medium, culturing period) at each differentiation stage, and the like, and by appropriately modifying or altering these methods as necessary.

<Human Erythroid Progenitor Cells, Human Blood Stem Cells>

As described above, the expression of the HPV-E6/E7 genes is necessary for the growth of the erythroid progenitor cell line. Nonetheless, it has been discovered for the first time by the present invention that the expression may be an inhibitory factor for differentiation of an erythroid progenitor cell line into enucleated red blood cells. It has been revealed for the first time that the expression of the HPV-E6/E7 genes needs to be switched from on to off from a period of maintaining the growth of an erythroid progenitor cell line to a period of forming enucleated red blood cells.

Thus, the present invention also provides the following human erythroid progenitor cell line capable of switching on and off of expression of the HPV-E6/E7 genes, and useful in the above-described method for producing human enucleated red blood cells.

A human erythroid progenitor cell line comprising an expression cassette capable of inducing expression of E6 and E7 genes of human papillomavirus type 16 in response to an external stimulus, wherein the human erythroid progenitor cell line grows in presence of an external stimulus and a blood growth factor and has a potential to produce human enucleated red blood cells by culturing in absence of the external stimulus.

Note that the "human erythroid progenitor cell line comprising an expression cassette capable of inducing expression of E6 and E7 genes of human papillomavirus type in response to an external stimulus" is a human erythroid progenitor cell line capable of stably expressing HPV-E6/E7 genes in the presence of an external stimulus as a result of introducing the expression cassette according to the present invention into the cells as in the case of the above-described human blood stem cells. From the viewpoint that the expression cassette according to the present invention can be removed together with the nuclei at the establishment stage of the cell line and further at the differentiation stage into human enucleated red blood cells described later, preferable is a human erythroid progenitor cell line comprising the expression cassette of the present invention incorporated into the genomic DNA.

The present invention also provides the following human erythroid stem cell useful in the above-described method for producing a human erythroid progenitor cell line.

A human erythroid stem cell comprising an expression cassette capable of inducing expression of E6 and E7 genes of human papillomavirus type 16 in response to an external stimulus.

The human blood stem cell and the human erythroid progenitor cell line of the present invention are preferably a cell derived from human pluripotent stem cells expressing a TAL1 gene from the viewpoint of more improved efficiency of inducing differentiation into blood cells (particularly erythroid cells). In addition, cells obtained by inducing differentiation of the human erythroid progenitor cell line and cells obtained by inducing differentiation of the human blood stem cells through the form of the human erythroid progenitor cell line include human enucleated red blood cells at a high ratio (for example, 62%) as described in Examples later.

Thus, the present invention also provides a human erythroid progenitor cell line or a human blood stem cell, which comprise an expression cassette capable of inducing expression of E6 and E7 genes of HPV type 16 in response to an external stimulus. The efficiency of inducing differentiation into human enucleated red blood cells is 30% or higher (preferably 40% or higher, more preferably 50% or higher, particularly preferably 60% or higher).

In the present invention, the "efficiency of inducing differentiation into human enucleated red blood cells" can be calculated, for example, by a method as described in Examples later. Specifically, nuclei of cells after differentiation induction into enucleated red blood cells and a marker for mature erythroid cells (for example, glycophorin A) are stained for analysis with a flow cytometer. Then, a ratio between the cells and cells positive for the marker for mature erythroid cells but negative for the nuclear staining is calculated. Thereby, a value of the "efficiency of inducing differentiation into human enucleated red blood cells" can be obtained.

<Method 1 for Utilizing Red Blood Cells Obtained by Method of the Present Invention>

As described above, according to the present invention, human enucleated red blood cells can be produced from the human pluripotent stem cells or human blood stem cells. Thus, it is possible to provide a large amount of red blood cells as a model of a red blood cell-related disease by preparing human pluripotent stem cells or blood stem cells from human with the disease and then inducing differentiation of these cells into human enucleated red blood cells by employing the method of the present invention. Examples of the "red blood cell-related disease" include hereditary spherocytosis, sickle-cell anemia, thalassemia, paroxysmal nocturnal hemoglobinuria, and megaloblastic anemia.

In addition, a drug candidate compound effective for treatment or prevention of red blood cell-related disease can be screened for by bringing the red blood cells thus prepared as a disease model into contact with a test compound, detecting the state of the red blood cells after the contact (for example, the shape, size, oxygen binding ability and releasing ability), and selecting a compound, which improves the state of the red blood cells.

The "test compound" used in the screening is not particularly limited. Examples thereof include an expression product from a gene library, a synthetic low-molecular-weight compound library, a peptide library, an antibody, a substance released by a bacterium, a liquid extract and a culture supernatant of cells (microorganisms, plant cells, animal cells), a purified or partially purified polypeptide, an extract derived from a marine organism, plant or animal, soil, and a random phage peptide display library.

The "contact" between the test compound and the red blood cells can be achieved, for example, by addition into a medium where the red blood cells obtained by the method of the present invention are cultured and maintained, or by administration into an experimental animal (preferably, immunodeficient animal) into which the red blood cells obtained by the method of the present invention are transplanted.

The state of the red blood cells after the contact with the test compound can be detected by a method known to those skilled in the art. For example, the shape and the size of the red blood cells can be detected through observation under a microscope or flow cytometry analysis, and the oxygen binding ability and releasing ability of the red blood cells can be detected by utilizing a commercially available analyzer.

Whether the state of the red blood cells is "improved" or not can be judged, for example: for hereditary spherocytosis, according to whether or not the shape of the red blood cells has changed from a sphere shape to a disk shape of normal red blood cells or a similar shape; for sickle-cell anemia, whether or not the shape of the red blood cells has changed from a sickle shape to a disk shape of normal red blood cells or a similar shape; and for sickle-cell anemia, thalassemia, and the like, whether or not the oxygen binding ability and releasing ability of the red blood cells have improved.

<Method 2 for Utilizing Red Blood Cells Obtained by Method of the Present Invention>

As another type of the red blood cell-related disease, infectious diseases are known. Particularly, malaria is an infectious disease caused by malarial parasites. The parasites divide and grow by asexual reproduction in a red blood cell, then destroy the red blood cell, and invade another red blood cell. As such a cycle is repeated, a symptom of high fever, renal failure, or the like occurs.

As described above, the present invention can provide a large amount of red blood cells where malarial parasites grow. Thus, the present invention can also provide a screening method for a drug candidate compound effective for treatment or prevention of malaria diseases. In this method, in the presence of a test compound, the red blood cells are brought into contact with malarial parasites, and the number of malarial parasites in the red blood cells after the contact is detected to select a compound, which has reduced the number of malarial parasites in the red blood cells in comparison with one in the absence of the test compound.

Examples of the "malarial parasites" include *Plasmodium falciparum, Plasmodium vivax, Plasmodium malariae,* and *Plasmodium ovale*, which belong to the Sporozoa. A method for bringing the red blood cells into contact with the malarial parasites and the test compound screened for are the same as those in the method 1 for utilizing the red blood cells.

The number of malarial parasites in the red blood cells after the contact with the test compound can be detected by a method known to those skilled in the art. Examples of the known method include a method in which a Giemsa stain is used for observation under an optical microscope, a flow cytometry analysis using an antibody specific to the malarial parasites, and quantitative PCR using primers specific to the genome of the malarial parasites.

Moreover, the present invention can be used in screening for a compound effective for infectious diseases other than malaria, in which red blood cells are not directly invaded. For example, when the source of infection causing an infectious disease other than malaria is brought into contact with a test compound, the human pluripotent stem cells of the present invention or human enucleated red blood cells produced from the human blood stem cells are added thereto, and thereby a situation can be constructed, which is a replicate of an environment similar to a human body. The experimental system may be in vitro or in vivo, and this situation allows screening for a compound, which reduces the number of the sources of infection.

<Method 3 for Utilizing Red Blood Cells Obtained by Method of the Present Invention>

It is also possible to determine whether or not a test compound adversely influences the red blood cells obtained by the method of the present invention, by bringing the red blood cells into contact with the test compound and detecting the state of the red blood cells after the contact (for example, the shape, size, oxygen binding ability and releasing ability).

The "test compound" in such a determination is not particularly limited as in the case of the above-described methods for utilizing the red blood cells. For example, using current or developing drugs (such as anti-cancer agents, immunosuppressants, anti-viral agents), whether these drugs have a side effect on the red blood cells can be determined.

A method for bringing the red blood cells into contact with the test compound and the test compound screened for, and the detection of the state of the red blood cells are the same as those in the method 1 for utilizing the red blood cells.

By the contact with the test compound, for example, when the red blood cells of a disk shape having a thickness of 1 to 3 μm and a diameter of 5 to 10 μm with the center depressed are deformed so that the red blood cells after the contact have another shape or size, it is possible to determine that the test compound be a compound adversely influencing the red blood cells. The "deformation into another shape" means to include not only deformation into a sphere shape or the like, but also rupturing of the membrane of the red blood cells leading to hemolysis.

Further, by the contact with the test compound, for example, when the oxygen binding ability and releasing ability of the red blood cells become lower than those of the red blood cells before the contact, it is possible to determine that the test compound be a compound adversely influencing the red blood cells.

EXAMPLES

Hereinafter, the present invention will be described more specifically based on Examples. However, the present invention is not limited to the following Examples. Meanwhile, the following cells, culture solutions, and vectors used for transfection were used in the present Examples.

<Cells>

Human umbilical cord blood-derived blood stem/progenitor cells (CD34-positive cells) were purchased from Cell Bank, RIKEN BioResource Center (RIKEN cell designation: C34).

As human iPS cells, amnion-derived iPS cell lines (HiPS-RIKEN-3A and HiPS-RIKEN-4A) established by the present inventors at Cell Bank, RIKEN BioResource Center were used. These cells were maintained by culturing on feeder cells, which are described below, in a basic fibroblast growth factor (b-FGF)-containing medium for primate ES cells (see Fujioka T. et al, Human Cell, 2010, vol. 23, pp. 113 to 118).

SNL76/7 cells purchased from ECACC were used as the feeder cells for maintenance culture for the human iPS cells. Further, MEF was also used as the feeder cells for maintenance culture for the human iPS cells. The present inventors prepared this MEF from a mouse fetus by standard technique and approach. These feeder cells for the maintenance culture for the human iPS cells were maintained by culturing in a 10% FBS-containing Dulbecco's modified Eagle's medium (DMEM) solution.

In addition, OP9 cells purchased from Cell Bank, RIKEN BioResource Center (RIKEN cell designation: RCB1124) were used as feeder cells for differentiation induction into blood cells. The cells were maintained by culturing in a 20% FBS-containing alpha minimum essential Eagle medium (α-MEM) solution.

<Culture Solutions>

As a culture solution used in a process of establishing an erythroid progenitor cell line (HUDEP) from the human umbilical cord blood-derived blood stem/progenitor cells, a serum-free medium (product name: STEMSPAN® SFEM culture solution, manufactured by STEMCELL THECHNOLOGIES INC) was used for growth of the human hematopoietic stem cells/progenitor cells.

The composition of a culture solution used in a process of inducing differentiation of human iPS cells into blood stem/progenitor cells and a process of establishing an erythroid progenitor cell line using the blood stem/progenitor cells induced and differentiated from the human iPS cells (hereinafter, referred to as "blood stem/progenitor cell-differentiation induction culture solution") was as follows.

An IMDM solution (manufactured by SIGMA-ALDRICH CO.) containing 15% FBS (manufactured by SIGMA-ALDRICH CO.), ITS liquid medium supplement (10 μg/ml human insulin, 5.5 μg/ml human transferrin, 5 ng/ml sodium selenite) (manufactured by SIGMA-ALDRICH CO.), 50 mg/ml ascorbic acid (manufactured by SIGMA-ALDRICH CO.), 0.45 mM alpha-monothioglycerol (manufactured by SIGMA-ALDRICH CO.), and 2 mM L-glutamine (manufactured by SIGMA-ALDRICH CO.).

The compositions of (two) culture solutions used to obtain enucleated red blood cells from the erythroid progenitor cell line were as follows.

[Culture Solution 1 for Producing Enucleated Red Blood Cells]

An IMDM solution (manufactured by SIGMA-ALDRICH CO.) containing 0.5% human plasma protein fraction (manufactured by Baxter International Inc.), 14.57 mg/ml D-mannitol (manufactured by SIGMA-ALDRICH CO.), 0.14 mg/ml adenine (manufactured by SIGMA-ALDRICH CO.), 0.94 mg/ml sodium hydrogen phosphate (manufactured by SIGMA-ALDRICH CO.), and 1 μM mifepristone (glucocorticoid receptor antagonist, manufactured by SIGMA-ALDRICH CO.) (see Miharada K. et al., Nature Biotechnology, 2006, vol. 24, no. 10, pp 1255 to 1256).

[Culture Solution 2 for Producing Enucleated Red Blood Cells]

An IMDM solution (manufactured by SIGMA-ALDRICH CO.) containing 10% human type AB serum (manufactured by Kohjin Bio Co., Ltd.), 20 ng/ml α-tocopherol (manufactured by SIGMA-ALDRICH CO.), 4 ng/ml linoleic acid (manufactured by SIGMA-ALDRICH CO.), 200 ng/ml cholesterol (manufactured by SIGMA-ALDRICH CO.), 2 ng/ml sodium selenite (manufactured by SIGMA-ALDRICH CO.), 200 μg/ml human holo-transferrin (manufactured by SIGMA-ALDRICH CO.), 10 μg/ml human insulin (manufactured by SIGMA-ALDRICH CO.), 10 μM ethanolamine (manufactured by SIGMA-ALDRICH CO.), 0.1 mM 2-mercaptoethanol (2-ME, manufactured by SIGMA-ALDRICH CO.), 14.57 mg/ml D-mannitol (manufactured by SIGMA-ALDRICH CO.), 1 μM mifepristone (manufactured by SIGMA-ALDRICH CO.), and 5 IU/ml EPO (modified from the composition described in Miharada K. et al, Nature Biotechnology, 2006, vol. 24, no. 10, pp. 1255 to 1256).

<Vectors>

In order to introduce a TAL1 gene into the human iPS cells, a CSII-EF-RfA lentiviral vector was used. Further, in order to introduce human papillomavirus E6/E7 (HPV-E6/E7) genes and a gene for encoding a tetracycline transactivator (rtTA) in a step of establishing an erythroid progenitor cell line described later, a CSIV-TRE-RfA-UbC-KT lentiviral vector was used. Both of CSII-EF-RfA and CSIV-TRE-RfA-UbC-KT were obtained by Subteam for Manipulation of Cell Fate, RIKEN BioResource Center. Furthermore, lentiviruses prepared using these lentiviral vectors by employing standard technique and approach. SEQ ID NOs: 1 and 3 respectively show the base sequences of the introduced human TAL1 gene and HPV-E6/E7 genes.

Note that it has been reported that the efficiency of inducing differentiation into blood cells is improved by forcibly expressing TAL1 in non-human primate ES cells (see Kurita R. et al, Stem Cells, 2006, vol. 24, pp. 2014 to 2022). Based on such a finding, the present inventors induced differentiation of the human iPS cells into erythroid progenitor cells by methods of Examples 2 and described later without inducing expression of HPV-E6/E7. As a result, although unillustrated, immortalized erythroid progenitor cell lines were established by such methods. However, enucleated red blood cells were not obtained from these cell lines.

In addition, it has been revealed that introducing HPV-E6/E7 oncogenes into CD36-positive erythroid progenitor cells can provide a cell line, which grows in a cytokine-dependent manner. Nevertheless, it is also reported that the efficiency of inducing differentiation of such a cell line into erythroid cells was significantly low (see Wong. S et al., Exp Hematol., 2010, vol. 38, no. 11, pp. 994 to 1005).

Example 1

Establishment of Erythroid Progenitor Cell Lines from Human Umbilical Cord Blood-Derived Blood Stem/Progenitor Cells In the presence of 50 ng/ml blood growth factors (SCF (manufactured by R&D Systems, Inc.), 50 ng/ml human thrombopoietin (TPO, manufactured by R&D Systems, Inc.), and 50 ng/ml human FLT3 ligand (FLT3-L, manufactured by R&D Systems, Inc.)), $1 \times 10^5$ human umbilical cord blood-derived blood stem/progenitor cells (CD34-positive cells) were cultured overnight (cultured at 37° C. in 5% $CO_2$. In all of the culture systems below, culturing was carried out under the same temperature and $CO_2$ concentration conditions).

Then, the above-described lentivirus enclosing a gene structure (construct) capable of adjusting expression of HPV-E6/E7 in an induction expression system (in which the expression was induced in the presence of doxycycline (DOX) but the expression was suppressed in the absence thereof) was introduced into the human umbilical cord blood-derived blood stem/progenitor cells.

The culturing was continued for 6 days after the introduction in a STEMSPAN® SFEM culture solution containing 50 ng/ml SCF, 3 U/ml EPO (manufactured by KIRIN Brewery Company, Limited) and $10^{-6}$ M DEX (manufactured by SIGMA-ALDRICH CO.).

Subsequently (Day 7 and later after the introduction), in order to induce expression of HPV-E6/E 1 µg/ml DOX was further added, and the culturing was carried out. Thereafter, the medium was regularly replaced (approximately twice a week), and the culturing was continued.

As a result of such culturing, it was found out that subculturing (cell growth maintenance) was possible for 6 months or longer after the introduction, and that human erythroid progenitor cell lines (HUDEP: human umbilical cord blood-derived erythroid progenitor cell lines) were established with reproducibility.

Example 2

Establishment of Erythroid Progenitor Cell Lines from Human iPS Cells

First, a transcription factor TAL1 was forcibly introduced into the human iPS cells using the above-described lentivirus, and human iPS cell lines were established which constantly expressed TAL1 (iPS-TAL1 cells).

Onto OP9 cells having been exposed to gamma radiation in advance, 4 to $8 \times 10^4$ iPS-TAL1 cells thus established was seeded and cultured for 10 days in the blood stem/progenitor cell-differentiation induction culture solution containing 200 ng/ml human insulin-like growth factor II (IGF-II, manufactured by R&D Systems, Inc.) and 20 ng/ml human vascular endothelial growth factor (VEGF, manufactured by R&D Systems, Inc.) to induce blood cells.

Ten days after the differentiation induction into the blood cells was started, 50 ng/ml SCF, 3 U/ml EPO, and $10^{-6}$ M DEX were added to the blood stem/progenitor cell-differentiation induction culture solution without IGF-II and VEGF. Further, the culturing was carried out for 6 days. Thereby, erythroid cells were induced.

On Day 16 after the differentiation induction into the blood cells was started, the above-described lentivirus enclosing the construct capable of adjusting expression of HPV-E6/E7 in the induction expression system was introduced.

For 4 days after the introduction (for 16 to 20 days after the differentiation induction into the blood cells was started), the culturing was continued in the presence of 50 ng/ml SCF, 3 U/ml EPO, and $10^{-6}$ M DEX.

Subsequently (Day 20 and later after the differentiation induction was started), in order to induce expression of HPV-E6/E7, 1 µg/ml DOX was further added, and the culturing was carried out. Thereafter, the medium was regularly replaced (approximately twice a week), and the culturing was continued.

Thus, as a result of such culturing, it was found out that subculturing (cell growth maintenance) was possible for 6 months or longer after the differentiation induction into the blood cells was started, and that human erythroid progenitor cell lines (HiDEP: human iPS cell-derived erythroid progenitor cell line) were established with reproducibility.

Moreover, in the process of establishing HiDEP, the culturing was carried out on the feeder cells (OP9 cells) as described above. However, it was found out that 3 months later after the differentiation induction into the blood cells was started, all of HiDEP thus obtained became cells capable of growing in the absence of the feeder cells.

<Evaluation of Properties of Human Erythroid Progenitor Cell Lines of the Present Invention: Part 1>

Figure 2:
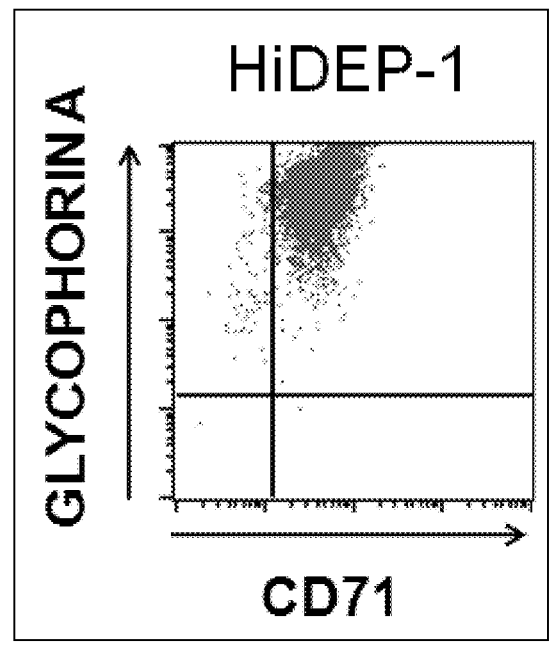
FIG. 2 is a plot chart for illustrating the result of analyzing, with a flow cytometer, expression of CD71 and glycophorin A in a cell line (HiDEP) of human erythroid progenitor cells obtained from human iPS cell-derived blood stem cells by the production method of the present invention.

In the human erythroid progenitor cell lines of the present invention, the expression of molecules specific to erythroid cells was examined. Specifically, expression of CD71 (transferrin receptor) and glycophorin A in three HUDEP lines established in Example 1 and five HiDEP lines established in Example 2 was examined by standard technique and approach using commercially available flow cytometer equipment and commercially available antibody. FIGS. 1 and 2 respectively show the results of HUDEP-1 and HiDEP-1 as typical examples of the obtained results.

Note that CD71 is a molecule whose expression has been confirmed in erythroid progenitor cells. It has also been revealed that CD71 is not expressed in mature erythroid cells. Meanwhile, glycophorin A is known to be expressed in both erythroid progenitor cells and mature erythroid cells.

As shown in FIGS. 1 and 2, it was found out that both HUDEP-1 and HiDEP-1 were erythroid cell lines at the differentiation stage and expressed the molecules specific to erythroid cells (CD71 and glycophorin A). Particularly, HiDEP-1 was cells expressing glycophorin A at a high level, suggesting that HiDEP-1 be mature erythroid cells in comparison with HUDEP-1 because.

Figure 3:
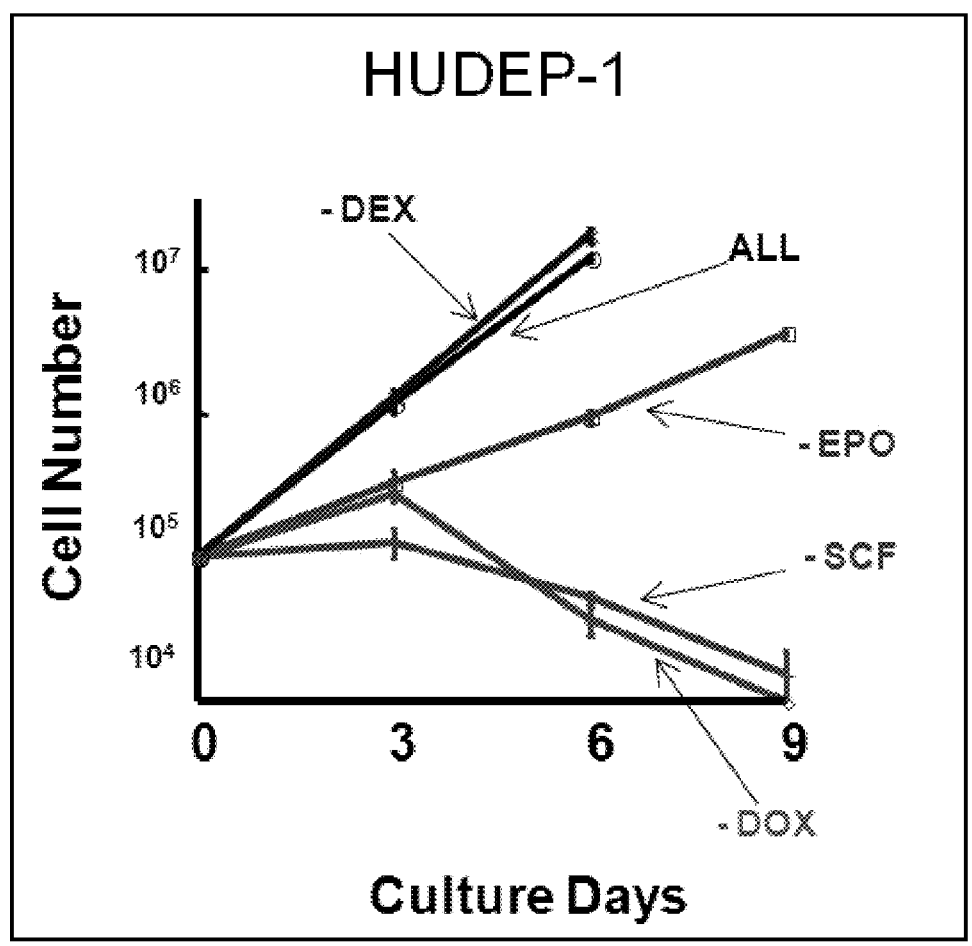
FIG. 3 is a graph for illustrating the result of analyzing the dependency of HUDEP growth on blood growth factors (SCF, EPO, and DEX) and DOX (external stimulus to induce expression of HPV-E6/E7 genes).
Figure 4:
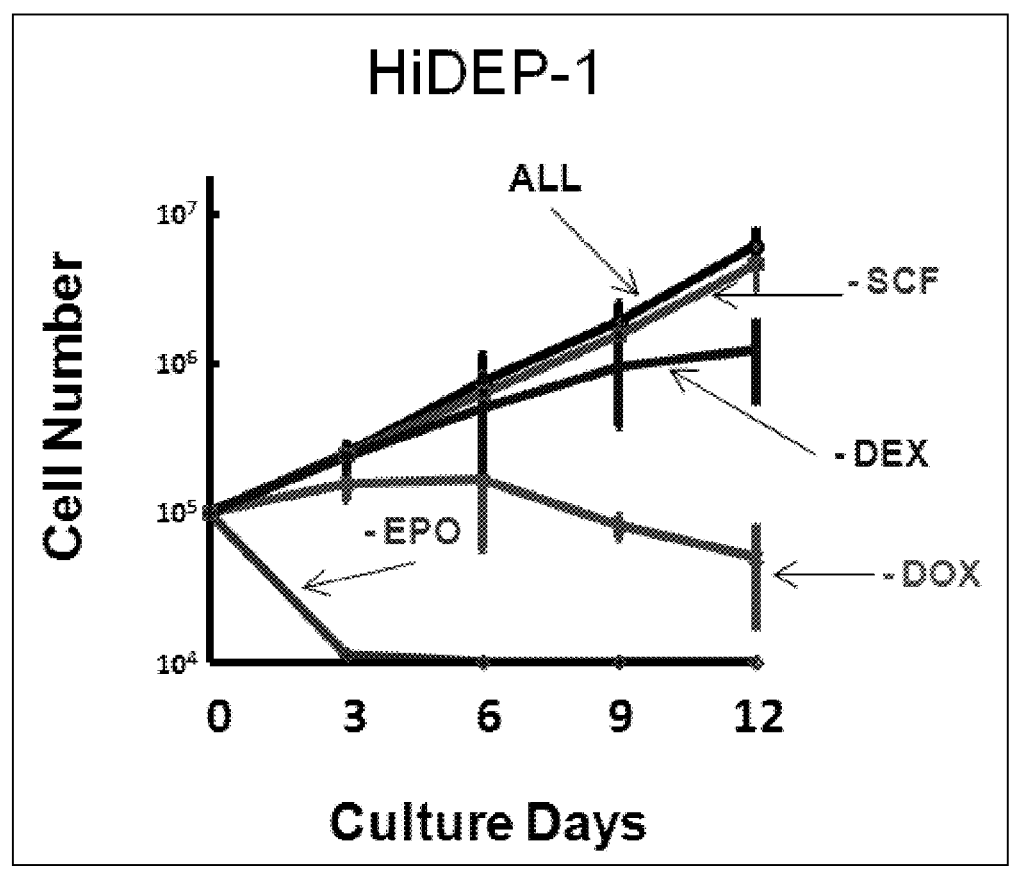
FIG. 4 is a graph for illustrating the result of analyzing the dependency of HiDEP growth on the blood growth factors and DOX.

Next, the growth factor dependency of the human erythroid progenitor cell lines of the present invention was examined. Specifically, the three HUDEP lines and the five HiDEP lines were cultured for 9 to 12 days in a STEMSPAN® SFEM culture solution and the blood stem/progenitor cell-differentiation induction culture solution, which contained the following combinations of growth factors. The change in cell count was examined. FIGS. 3 and 4 show typical examples of the obtained results.

ALL: all factors (DOX (HPV-E6/E7), SCF, EPO, and DEX)

"−DOX": DOX absent (SCF, EPO, and DEX)

"−SCF": SCF absent (DOX (HPV-E6/E7), EPO, and DEX)
"−EPO": EPO absent (DOX (HPV-E6/E7), SCF, and DEX)
"−DEX": DEX absent (DOX (HPV-E6/E7), SCF, and EPO).

As shown in FIGS. 3 and 4, it was found out that all of the three HUDEP lines and the five HiDEP lines were cells capable of growing only under a condition where HPV-E6/E7 were expressed.

Moreover, as shown in FIG. 3, it was also revealed that SCF was also essential for the growth of HUDEP-1, and further that although EPO was not essential, the growth of HUDEP-1 was improved in the presence of EPO. Furthermore, as shown in FIG. 4, it was revealed that the growth of HiDEP-1 was dependent on EPO also.

Thus, it was revealed that the expression of HPV-E6/E7 and at least any one blood growth factor were essential for the growth of the human erythroid progenitor cell lines of the present invention.

Example 3

Differentiation Induction of Mature Erythroid Cells from Human Erythroid Progenitor Cell Lines of the Present Invention (Production of Enucleated Red Blood Cells)

As described above, HPV-E6/E7 and SCF are essential for the growth of HUDEP. Moreover, HPV-E6/E7 and EPO are essential for the growth of HiDEP. It has been known that, in the differentiation and maturation processes of red blood cells, the cell division potential is gradually decreased from the stage of erythroid progenitor cells, and orthochromatic erythroblasts before enucleation at the final stage lose the cell division potential completely. Thus, based on the above-described findings, it was thought that differentiation induction of the human erythroid progenitor cell lines of the present invention into efficiently matured erythroid cells (including enucleated red blood cells) was possible under a condition excluding HPV-E6/E7 and the blood growth factors essential for the growth of these.

Thus, it was attempted for HUDEP that HUDEP be cultured in the culture solution 2 for producing enucleated red blood cells excluding SCF and DOX serving as the condition for inducing the expression of HPV-E6/E7 so as to induce differentiation into mature erythroid cells (including enucleated red blood cells). Moreover, it was attempt for HiDEP that HiDEP be cultured in the culture solution 1 for producing enucleated red blood cells excluding EPO and DOX so as to induce differentiation into mature erythroid cells (including enucleated red blood cells).

As a result, when the established human erythroid progenitor cell lines (HUDEP and HiDEP) were cultured under a condition where HPV-E6/E7 were not expressed and in the absence of the respective blood growth factors essential for the cell growth, differentiation induction into more matured erythroid cells was observed in any cell line.

Figure 5:
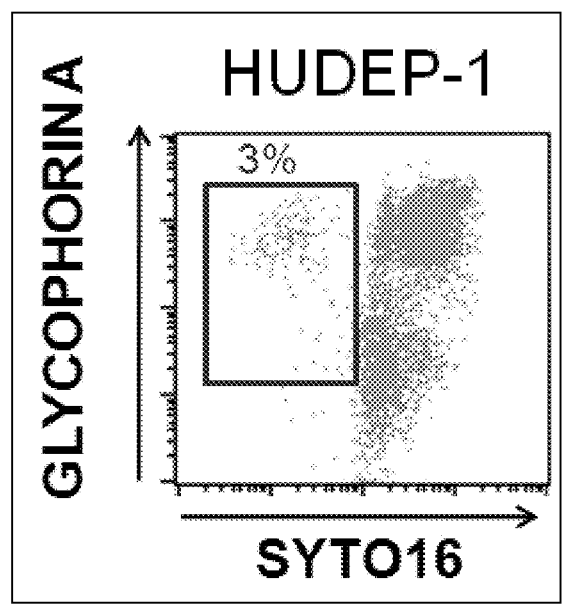
FIG. 5 is a plot chart for illustrating the result of analyzing, with a flow cytometer, a ratio of cells (enucleated red blood cells) positive for glycophorin A but negative for nuclear staining (SYTO16) in HUDEP after differentiation induction into the enucleated red blood cells.
Figure 6:
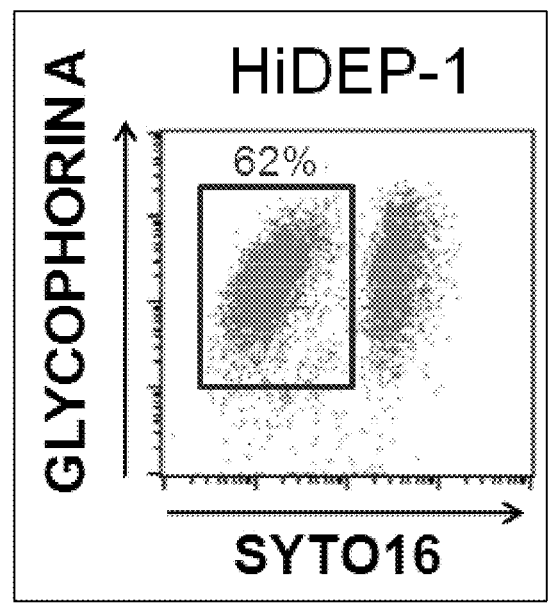
FIG. 6 is a plot chart for illustrating the result of analyzing, with a flow cytometer, a ratio of cells (enucleated red blood cells) positive for glycophorin A but negative for nuclear staining in HiDEP after differentiation induction into the enucleated red blood cells.

Further, examined were ratios of enucleated red blood cells in the human erythroid progenitor cell lines of the present invention after the differentiation induction into mature erythroid cells. Specifically, the expression of glycophorin A and presence or absence of nuclear staining in HUDEP-1 and HiDEP-1 on Day 5 after the differentiation induction into mature erythroid cells were examined by standard technique and approach using commercially available flow cytometer equipment, commercially available antibody, and a nuclear staining solution (SYTO16). FIGS. 5 and 6 show the obtained result.

Note that glycophorin A is a marker for mature erythroid cells. In addition, SYTO16 is a staining solution, which permeates through the membrane of living cells and stains the nuclei. Thus, SYTO16-positive cells mean cells having nuclei, and negative cells mean cells not having nuclei (enucleated red blood cells).

As apparent from the results shown in FIGS. 5 and 6, in both HUDEP and HiDEP, cells several days (5 days) after the differentiation induction into mature erythroid cells included enucleated red blood cells. Particularly, it was found out that after the differentiation induction into mature erythroid cells, HiDEP-1 cells produced enucleated red blood cells at quite a high ratio of approximately 60%.

<Evaluation of Properties of Human Erythroid Progenitor Cell Lines of the Present Invention: Part 2>

Figure 7:
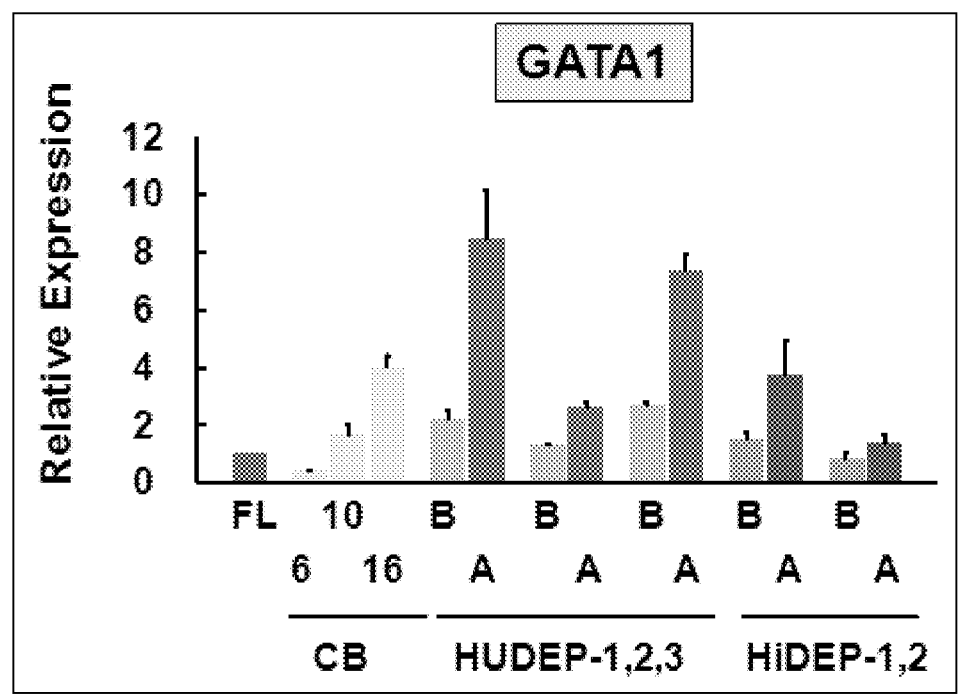
FIG. 7 is a graph for illustrating the result of analyzing levels of a GATA1 gene expressed in three HUDEP lines (HUDEP-1, HUDEP-2, and HUDEP-3) and two HiDEP lines (HiDEP-1 and HiDEP-2). Note that, in the graph, a relative expression level is a value obtained when the level of expression in human fetal liver-derived cells (FL) is taken as 1.

GATA1 has been revealed to be a transcription factor essential for final differentiation and maturation of red blood cells and the like. Thus, levels of a GATA1 gene expressed in the differentiation process of the human erythroid progenitor cell lines of the present invention into mature erythro id cells were examined. Specifically, mRNAs were extracted from cells of each of three HUDEP lines (HUDEP-1, HUDEP-2, and HUDEP-3) and two HiDEP lines (HiDEP-1 and HiDEP-2) before and after differentiation induction into mature erythro id cells by standard approach using a commercially available reagent. Then, reverse transcription was performed using these mRNAs as templates. Then, quantitative RT-PCR was performed using the obtained cDNAs as templates and using commercially available quantitative PCR instrument and reagent to examine the level of the GATA1 gene expressed in each cell. Moreover, the analysis of GATA1 gene expression was also performed in human fetal liver-derived cells (FL) and cells on Days 6, 10, and 16 after differentiation induction into erythroid cells from blood stem cells in umbilical cord blood (CB 6, 10, 16) as controls. Note that it has been known that the fetal liver includes erythroid progenitor cells abundantly. In addition, the differentiation induction into erythroid cells from blood stem cells in umbilical cord blood was performed according to the method described in Miharada K. et al, Nature Biotechnology, 2006, vol. 24, no. 10, pp. 1255 to 1256. FIG. 7 shows the obtained result. In the graph, "B" shows the result of analyzing the cells before the differentiation induction into mature erythroid cells, and "A" shows the result of analyzing the cells after the differentiation induction into mature erythroid cells.

As shown in FIG. 7, in HUDEP-1, HUDEP-2, HUDEP-3, HiDEP-1, and HiDEP-2, the GATA1 gene was expressed to some degree before the differentiation induction into erythroid cells. It was found out that these expressions were increased after the differentiation induction.

Figure 8:
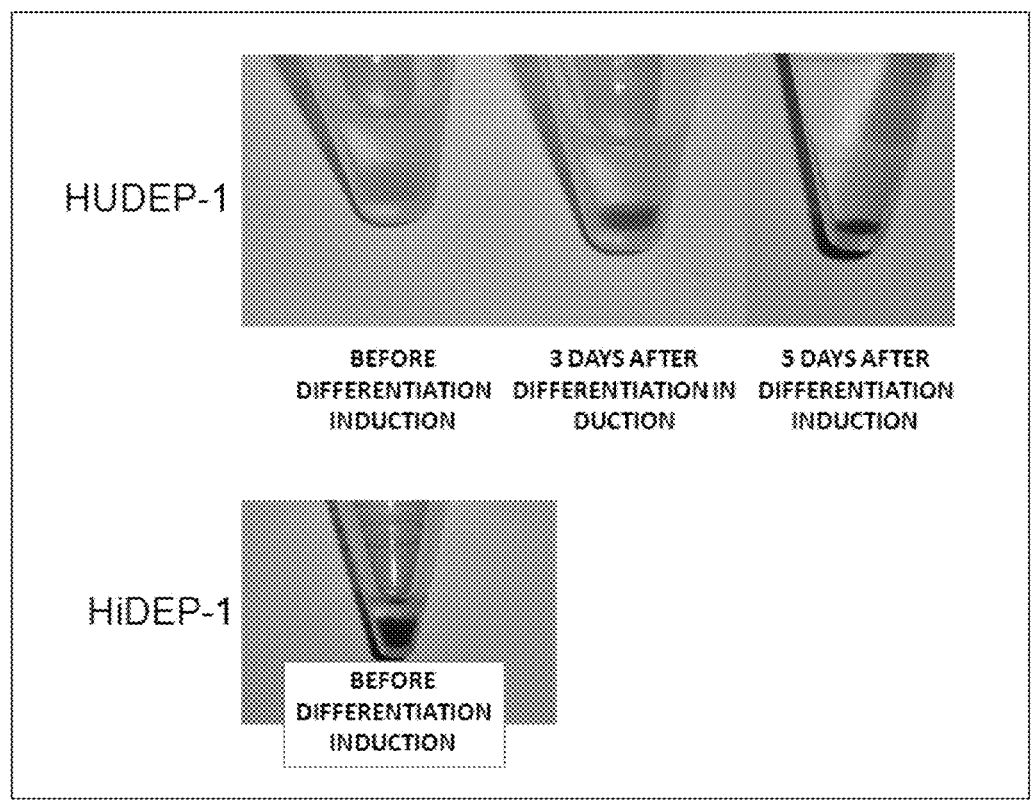
FIG. 8 shows photographs for illustrating the result of visually observing HUDEP-1 and HiDEP-1 cell precipitations to evaluate amounts of hemoglobin synthesized.

Next, hemoglobin synthesis was examined in the differentiation process of the human erythroid progenitor cell lines of the present invention into mature erythroid cells. Specifically, based on the fact that cell precipitations become more reddish as more hemoglobins are synthesized, the color of the cell precipitations of each of the above three HUDEP lines and five HiDEP lines before and after differentiation induction into more matured erythroid cells was visually observed. As typical examples of the obtained results, FIG. 8 shows the results of HUDEP-1 and HiDEP-1.

It was found out that the three HUDEP lines and the five HiDEP lines constantly produced hemoglobins, although there was a difference in a synthesized amount among the cell lines. As shown in FIG. 8, for example, HUDEP-1 showed a slightly pink color before the differentiation induction into more matured erythroid cells, and the color changed to a clear red color after the differentiation induction. This revealed that hemoglobins were synthesized abundantly. Moreover, as to HiDEP-1, even before the differentiation induction into more matured erythroid cells (in the maintenance culture), clearly red cell precipitations were always observed. This revealed that hemoglobins are always abundantly synthesized.

Figure 9:
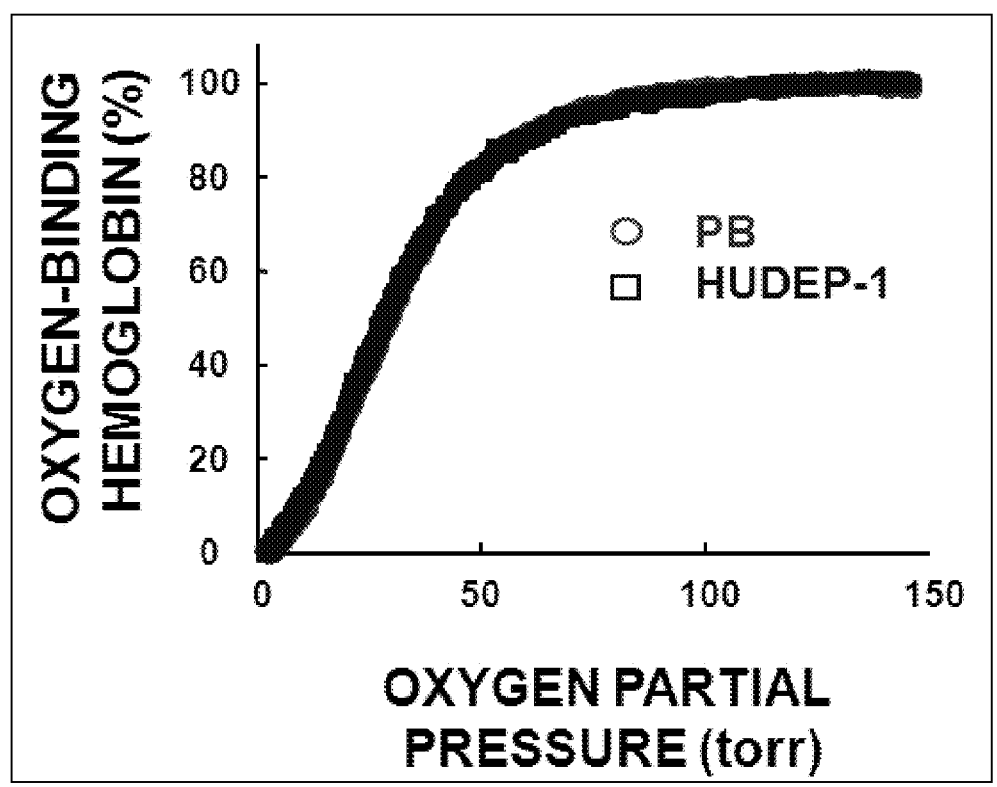
FIG. 9 is a graph for illustrating the result of analyzing the oxygen binding and releasing ability of HUDEP-1.
Figure 10:
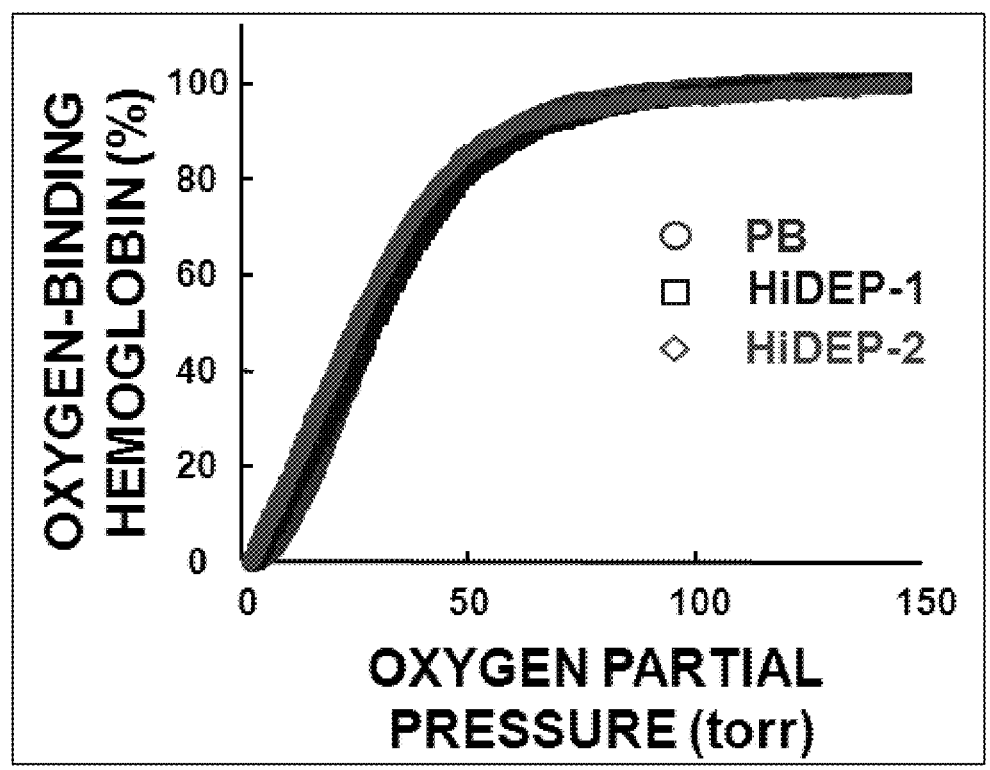
FIG. 10 is a graph for illustrating the result of analyzing the oxygen binding and releasing ability of HiDEP-1 and HiDEP-2.

Next, hemoglobins synthesized in the human erythro id progenitor cell lines of the present invention were analyzed in terms of oxygen binding and releasing ability. Specifically, the oxygen binding and releasing ability of hemoglobins in cells of each HUDEP-1, HiDEP-1, and HiDEP-2 was analyzed by standard technique and approach using a commercially available analyzer for oxygen binding and releasing ability. Moreover, the oxygen binding and releasing ability of hemoglobins in adult peripheral blood (normal red blood cells) was also analyzed as a control. FIGS. 9 and 10 show the obtained result.

As apparent from the result shown in FIGS. 9 and 10, the ability of both HUDEP and HiDEP to release oxygen in a low oxygen condition and bind to oxygen in a high oxygen condition was similar to that of normal blood (see "PB" in the graphs). Thus, it was found out that the hemoglobins synthesized in the human erythroid progenitor cell lines of the present invention had a similar function to that in the normal red blood cells.

As described above, the present invention makes it possible to provide a method for producing an immortalized human erythroid progenitor cell line, enabling efficient and stable production of enucleated red blood cells; and a method for producing human enucleated red blood cells from a human erythroid progenitor cell line obtained by the aforementioned production method.

Thus, since having hemoglobins with an oxygen binding and releasing ability equivalent to that of normal red blood cells, enucleated red blood cells obtained by the production methods of the present invention are useful for treatment of bleeding by trauma or during operation, anemia, and blood diseases such as sickle-cell anemia and hemolytic disease.

Particularly, when a Type O RhD(−) human erythroid progenitor cell line is established by the methods of the present invention, red blood cells produced from the cell line can be used for 99% or more of humans. In normal transfusion, the ABO type is matched by taking into consideration that host red blood cells are destroyed by anti-A and anti-B antibodies mixed therein. Nevertheless, when red blood cells are produced in vitro from a human erythroid progenitor cell line (immortalized cell line), no antibody is produced. Hence, red blood cells not expressing major antigens (A, B, RhD), that is, type O RhD(−) red blood cells, can be used for 99% or more of humans.

Moreover, the methods of the present invention make it possible to produce enucleated red blood cells from pluripotent stem cells. Thus, when an erythroid progenitor cell line (immortalized cell line) is established by the methods of the present invention from iPS cells prepared using cells (skin cells, blood, or the like) of a patient having a special blood type, a stable blood supply system can be constructed for the patient having a special blood type (person with type Rh-null, type -D-, or the like) without a red blood cell antigen most people in the world have.

The human erythroid progenitor cell line and so forth of the present invention have HPV-E6/E7 oncogenes introduced therein, whose expression is controlled by an external stimulus. Nonetheless, the oncogenes are introduced in the cell nuclei and lost during enucleation.

Further, when enucleated red blood cells are produced from a human erythroid progenitor cell line, it is technically difficult to make the enucleation efficiency perfectly 100%. In the enucleated red blood cells, nucleated cells (original human erythroid progenitor cells and the like) remain more or less. Nevertheless, since the diameter of enucleated red blood cells is as small as 10 µm or less, enucleated red blood cells can be selected by removing nucleated cells with an already generally-adopted leukocyte reduction filter or the like.

Even when enucleated red blood cells are selected by such a method, it is still difficult to remove nucleated cells 100%, and nucleated cells seem to remain in some degree. The nucleated cells thus remaining can be eliminated by radiation exposure (inducing cell death). The elimination of nucleated cells by radiation exposure (removal of white blood cells) is an already-clinically commonly-used technique in red blood cell-transfusion for particular cases.

As described above, in the method for producing human enucleated red blood cells of the present invention, the HPV-E6/E7 oncogene are lost at the final production stage. Further, in combination with the above-described method for removing nucleated cells, a risk of tumorigenesis in human erythroid progenitor cell line and the like can be completely eliminated.

Furthermore, by thoroughly inspecting an erythroid progenitor cell line established by the methods of the present invention for whether the source of infection (such as hepatitis viruses or AIDS viruses) is not mixed into the cell line, the present invention makes it possible to construct a supply system of red blood cells usable for various purposes and quite highly safe.

What is claimed is:

1. A method for producing a human erythroid progenitor cell line for producing human enucleated red blood cells, the method comprising the steps of:
   introducing into human hematopoietic stem cells an expression cassette comprising E6 and E7 genes of human papillomavirus type 16 operably linked to a promoter responsive to an added external stimulus;
   culturing the human hematopoietic stem cells having the expression cassette introduced therein in the presence of the external stimulus and at least one blood growth factor selected from the group consisting of SCF, EPO, TPO and DEX under conditions to produce human erythroid progenitor cells, and
   identifying human erythroid progenitor cells in the culture.

2. The method according to claim 1, wherein the human hematopoietic stem cells are cells obtained by inducing differentiation of human pluripotent stem cells expressing a TAL1 gene.

3. A human erythroid progenitor cell line comprising an expression cassette comprising E6 and E7 genes of human papillomavirus type 16 operably linked to a promoter responsive to an added external stimulus, wherein the human erythroid progenitor cell line grows in the presence of the external stimulus and at least one blood growth factor selected from the group consisting of SCF, EPO, TPO and DEX and produces human enucleated red blood cells by culturing in the absence of the external stimulus.

4. A method for producing human enucleated red blood cells, the method comprising the step of culturing the human erythroid progenitor cell line obtained by the method according to any one of claims 1 and 2 or the human erythroid progenitor cell line according to claim 3 in absence of the external stimulus.

5. A method for producing human enucleated red blood cells, the method comprising the steps of:
- introducing into human hematopoietic stem cells an expression cassette comprising E6 and E7 genes of human papillomavirus type 16 operably linked to a promoter responsive in response to an added external stimulus;
- culturing the human hematopoietic stem cells having the expression cassette introduced therein in the presence of the external stimulus and at least one blood growth factor selected from the group consisting of SCF, EPO, TPO and DEX, thereby inducing the expression of E6 and E7 genes of human papillomavirus type 16 in the cells and obtaining human erythroid progenitor cells; and
- culturing the human erythroid progenitor cells in absence of the external stimulus, thereby suppressing the expression of E6 and E7 genes of human papillomavirus type 16 in the cells and inducing the production of human enucleated red blood cells.

6. The method according to claim 5, wherein the human hematopoietic stem cells are cells obtained by inducing differentiation of human pluripotent stem cells expressing a TAL1 gene.

7. A human erythroid stem cell comprising an expression cassette comprising E6 and E7 genes of human papillomavirus type 16 operably linked to a promoter responsive to an added external stimulus.

8. The human erythroid stem cells according to claim 7, wherein the human hematopoietic stem cell is a cell obtained by inducing differentiation of human pluripotent stem cells expressing a TAL1 gene.

* * * * *

SEQUENCE LISTING

```
<160> NUMBER OF SEQ ID NOS: 5

<210> SEQ ID NO 1
<211> LENGTH: 996
<212> TYPE: DNA
<213> ORGANISM: Homo sapiens
<220> FEATURE:
<221> NAME/KEY: CDS
<222> LOCATION: (1)..(996)
<223> OTHER INFORMATION:

<400> SEQUENCE: 1 atg acc gag cgg ccg ccg agc gag gcg gct cgc agt gac ccc cag cta      48
Met Thr Glu Arg Pro Pro Ser Glu Ala Ala Arg Ser Asp Pro Gln Leu
1               5                   10                  15 gag gga cgg gac gcg gcc gag gcc agc atg gcc ccc ccg cac ctg gtc      96
Glu Gly Arg Asp Ala Ala Glu Ala Ser Met Ala Pro Pro His Leu Val
            20                  25                  30
```

```
ctg ctg aac ggc gtc gcc aag gag acg agc cgc gcg gcc gca gcg gag    144
Leu Leu Asn Gly Val Ala Lys Glu Thr Ser Arg Ala Ala Ala Ala Glu
        35                  40                  45 ccc cca gtc atc gaa ctg ggc gcg cgc gga ggc ccg ggg ggc ggc cct    192
Pro Pro Val Ile Glu Leu Gly Ala Arg Gly Gly Pro Gly Gly Gly Pro
    50                  55                  60 gcc ggt ggg ggc ggc gcc gcg aga gac tta aag ggc cgc gac gcg gcg    240
Ala Gly Gly Gly Gly Ala Ala Arg Asp Leu Lys Gly Arg Asp Ala Ala
65                  70                  75                  80 acg gcc gaa gcg cgc cat cgg gtg ccc acc acc gag ctg tgc aga cct    288
Thr Ala Glu Ala Arg His Arg Val Pro Thr Thr Glu Leu Cys Arg Pro
                85                  90                  95 ccc ggg ccc gcc ccg gcc ccc gcg ccc gcc tcg gtt aca gcg gag ctg    336
Pro Gly Pro Ala Pro Ala Pro Ala Pro Ala Ser Val Thr Ala Glu Leu
            100                 105                 110 ccc ggc gac ggc cgc atg gtg cag ctg agt cct ccc gcg ctg gct gcc    384
Pro Gly Asp Gly Arg Met Val Gln Leu Ser Pro Pro Ala Leu Ala Ala
        115                 120                 125 ccc gcc gcc ccc ggc cgc gcg ctg ctc tac agc ctc agc cag ccg ctg    432
Pro Ala Ala Pro Gly Arg Ala Leu Leu Tyr Ser Leu Ser Gln Pro Leu
    130                 135                 140 gcc tct ctc ggc agc ggg ttc ttt ggg gag ccg gat gcc ttc cct atg    480
Ala Ser Leu Gly Ser Gly Phe Phe Gly Glu Pro Asp Ala Phe Pro Met
145                 150                 155                 160 ttc acc acc aac aat cga gtg aag agg aga cct tcc ccc tat gag atg    528
Phe Thr Thr Asn Asn Arg Val Lys Arg Arg Pro Ser Pro Tyr Glu Met
                165                 170                 175 gag att act gat ggt ccc cac acc aaa gtt gtg cgg cgt atc ttc acc    576
Glu Ile Thr Asp Gly Pro His Thr Lys Val Val Arg Arg Ile Phe Thr
            180                 185                 190 aac agc cgg gag cga tgg cgg cag cag aat gtg aac ggg gcc ttt gcc    624
Asn Ser Arg Glu Arg Trp Arg Gln Gln Asn Val Asn Gly Ala Phe Ala
        195                 200                 205 gag ctc cgc aag ctg atc ccc aca cat ccc ccg gac aag aag ctc agc    672
Glu Leu Arg Lys Leu Ile Pro Thr His Pro Pro Asp Lys Lys Leu Ser
    210                 215                 220 aag aat gag atc ctc cgc ctg gcc atg aag tat atc aac ttc ttg gcc    720
Lys Asn Glu Ile Leu Arg Leu Ala Met Lys Tyr Ile Asn Phe Leu Ala
225                 230                 235                 240 aag ctg ctc aat gac cag gag gag gag ggc acc cag cgg gcc aag act    768
Lys Leu Leu Asn Asp Gln Glu Glu Glu Gly Thr Gln Arg Ala Lys Thr
                245                 250                 255 ggc aag gac cct gtg gtg ggg gct ggt ggg ggt gga ggt ggg gga ggg    816
Gly Lys Asp Pro Val Val Gly Ala Gly Gly Gly Gly Gly Gly Gly Gly
            260                 265                 270 ggc ggc gcg ccc cca gat gac ctc ctg caa gac gtg ctt tcc ccc aac    864
Gly Gly Ala Pro Pro Asp Asp Leu Leu Gln Asp Val Leu Ser Pro Asn
        275                 280                 285 tcc agc tgc ggc agc tcc ctg gat ggg gca gcc agc ccg gac agc tac    912
Ser Ser Cys Gly Ser Ser Leu Asp Gly Ala Ala Ser Pro Asp Ser Tyr
    290                 295                 300 acg gag gag ccc gcg ccc aaa cac acg gcc cgc agc ctc cat cct gcc    960
Thr Glu Glu Pro Ala Pro Lys His Thr Ala Arg Ser Leu His Pro Ala
305                 310                 315                 320 atg ctg cct gcc gcc gat gga gcc ggc cct cgg tga                    996
Met Leu Pro Ala Ala Asp Gly Ala Gly Pro Arg
                325                 330

<210> SEQ ID NO 2
```

<211> LENGTH: 331
<212> TYPE: PRT
<213> ORGANISM: Homo sapiens

<400> SEQUENCE: 2

```
Met Thr Glu Arg Pro Pro Ser Glu Ala Ala Arg Ser Asp Pro Gln Leu
1               5                   10                  15

Glu Gly Arg Asp Ala Ala Glu Ala Ser Met Ala Pro Pro His Leu Val
            20                  25                  30

Leu Leu Asn Gly Val Ala Lys Glu Thr Ser Arg Ala Ala Ala Ala Glu
        35                  40                  45

Pro Pro Val Ile Glu Leu Gly Ala Arg Gly Pro Gly Gly Gly Pro
    50                  55                  60

Ala Gly Gly Gly Ala Ala Arg Asp Leu Lys Gly Arg Asp Ala Ala
65                  70                  75                  80

Thr Ala Glu Ala Arg His Arg Val Pro Thr Thr Glu Leu Cys Arg Pro
                85                  90                  95

Pro Gly Pro Ala Pro Ala Pro Ala Pro Ala Ser Val Thr Ala Glu Leu
            100                 105                 110

Pro Gly Asp Gly Arg Met Val Gln Leu Ser Pro Pro Ala Leu Ala Ala
        115                 120                 125

Pro Ala Ala Pro Gly Arg Ala Leu Leu Tyr Ser Leu Ser Gln Pro Leu
    130                 135                 140

Ala Ser Leu Gly Ser Gly Phe Phe Gly Glu Pro Asp Ala Phe Pro Met
145                 150                 155                 160

Phe Thr Thr Asn Asn Arg Val Lys Arg Arg Pro Ser Pro Tyr Glu Met
                165                 170                 175

Glu Ile Thr Asp Gly Pro His Thr Lys Val Val Arg Arg Ile Phe Thr
            180                 185                 190

Asn Ser Arg Glu Arg Trp Arg Gln Gln Asn Val Asn Gly Ala Phe Ala
        195                 200                 205

Glu Leu Arg Lys Leu Ile Pro Thr His Pro Pro Asp Lys Lys Leu Ser
    210                 215                 220

Lys Asn Glu Ile Leu Arg Leu Ala Met Lys Tyr Ile Asn Phe Leu Ala
225                 230                 235                 240

Lys Leu Leu Asn Asp Gln Glu Glu Gly Thr Gln Arg Ala Lys Thr
                245                 250                 255

Gly Lys Asp Pro Val Val Gly Ala Gly Gly Gly Gly Gly Gly Gly
            260                 265                 270

Gly Gly Ala Pro Pro Asp Asp Leu Leu Gln Asp Val Leu Ser Pro Asn
        275                 280                 285

Ser Ser Cys Gly Ser Ser Leu Asp Gly Ala Ala Ser Pro Asp Ser Tyr
    290                 295                 300

Thr Glu Glu Pro Ala Pro Lys His Thr Ala Arg Ser Leu His Pro Ala
305                 310                 315                 320

Met Leu Pro Ala Ala Asp Gly Ala Gly Pro Arg
                325                 330
```

<210> SEQ ID NO 3
<211> LENGTH: 755
<212> TYPE: DNA
<213> ORGANISM: Human papillomavirus type 16
<220> FEATURE:
<221> NAME/KEY: CDS
<222> LOCATION: (1)..(456)
<223> OTHER INFORMATION:
<220> FEATURE:

<221> NAME/KEY: CDS
<222> LOCATION: (459)..(755)
<223> OTHER INFORMATION:

<400> SEQUENCE: 3

```
atg ttt cag gac cca cag gag cga ccc aga aag tta cca cag tta tgc        48
Met Phe Gln Asp Pro Gln Glu Arg Pro Arg Lys Leu Pro Gln Leu Cys
1               5                   10                  15 aca gag ctg caa aca act ata cat gat ata ata tta gaa tgt gtg tac        96
Thr Glu Leu Gln Thr Thr Ile His Asp Ile Ile Leu Glu Cys Val Tyr
                20                  25                  30 tgc aag caa cag tta ctg cga cgt gag gta tat gac ttt gct ttt cgg       144
Cys Lys Gln Gln Leu Leu Arg Arg Glu Val Tyr Asp Phe Ala Phe Arg
            35                  40                  45 gat tta tgc ata gta tat aga gat ggg aat cca tat gct gta tgt gat       192
Asp Leu Cys Ile Val Tyr Arg Asp Gly Asn Pro Tyr Ala Val Cys Asp
        50                  55                  60 aaa tgt tta aag ttt tat tct aaa att agt gag tat aga cat tat tgt       240
Lys Cys Leu Lys Phe Tyr Ser Lys Ile Ser Glu Tyr Arg His Tyr Cys
65                  70                  75                  80 tat agt ttg tat gga aca aca tta gaa cag caa tac aac aaa ccg ttg       288
Tyr Ser Leu Tyr Gly Thr Thr Leu Glu Gln Gln Tyr Asn Lys Pro Leu
                85                  90                  95 tgt gat ttg tta att agg tgt att aac tgt caa aag cca ctg tgt cct       336
Cys Asp Leu Leu Ile Arg Cys Ile Asn Cys Gln Lys Pro Leu Cys Pro
            100                 105                 110 gaa gaa aag caa aga cat ctg gac aaa aag caa aga ttc cat aat ata       384
Glu Glu Lys Gln Arg His Leu Asp Lys Lys Gln Arg Phe His Asn Ile
        115                 120                 125 agg ggt cgg tgg acc ggt cga tgt atg tct tgt tgc aga tca tca aga       432
Arg Gly Arg Trp Thr Gly Arg Cys Met Ser Cys Cys Arg Ser Ser Arg
    130                 135                 140 aca cgt aga gaa acc cag ctg taa tc atg cat gga gat aca cct aca       479
Thr Arg Arg Glu Thr Gln Leu        Met His Gly Asp Thr Pro Thr
145                 150                    155 ttg cat gaa tat atg tta gat ttg caa cca gag aca act gat ctc tac       527
Leu His Glu Tyr Met Leu Asp Leu Gln Pro Glu Thr Thr Asp Leu Tyr
        160                 165                 170 tgt tat gag caa tta aat gac agc tca gag gag gag gat gaa ata gat       575
Cys Tyr Glu Gln Leu Asn Asp Ser Ser Glu Glu Glu Asp Glu Ile Asp
    175                 180                 185                 190 ggt cca gct gga caa gca gaa ccg gac aga gcc cat tac aat att gta       623
Gly Pro Ala Gly Gln Ala Glu Pro Asp Arg Ala His Tyr Asn Ile Val
                195                 200                 205 acc ttt tgt tgc aag tgt gac tct acg ctt cgg ttg tgc gta caa agc       671
Thr Phe Cys Cys Lys Cys Asp Ser Thr Leu Arg Leu Cys Val Gln Ser
            210                 215                 220 aca cac gta gac att cgt act ttg gaa gac ctg tta atg ggc aca cta       719
Thr His Val Asp Ile Arg Thr Leu Glu Asp Leu Leu Met Gly Thr Leu
        225                 230                 235 gga att gtg tgc ccc atc tgt tct cag aaa cca taa                       755
Gly Ile Val Cys Pro Ile Cys Ser Gln Lys Pro
    240                 245
```

<210> SEQ ID NO 4
<211> LENGTH: 151
<212> TYPE: PRT
<213> ORGANISM: Human papillomavirus type 16

```
<400> SEQUENCE: 4

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 5
<211> LENGTH: 98
<212> TYPE: PRT
<213> ORGANISM: Human papillomavirus type 16

<400> SEQUENCE: 5

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```